United States Patent [19]
Buchholtz et al.

[11] Patent Number: 5,409,006
[45] Date of Patent: Apr. 25, 1995

[54] SYSTEM FOR THE TREATMENT OF PATHOLOGICAL TISSUE HAVING A CATHETER WITH A MARKER FOR AVOIDING DAMAGE TO HEALTHY TISSUE

[75] Inventors: Gerhard Buchholtz, Erlangen; Ulrich Schaetzle, Roettenbach, both of Germany

[73] Assignee: Siemens Aktiengesellschaft, Munich, Germany

[21] Appl. No.: 151,158

[22] Filed: Nov. 12, 1993

[30] Foreign Application Priority Data

Dec. 3, 1992 [DE] Germany ............... 42 40 722.2

[51] Int. Cl.⁶ ............................................. A61B 8/00
[52] U.S. Cl. .......................... 128/660.03; 601/3; 607/96; 607/97; 607/105
[58] Field of Search ........................... 601/2–4; 128/660.03; 607/96–105

[56] References Cited

U.S. PATENT DOCUMENTS

| | | |
|---|---|---|
| 4,497,324 | 2/1985 | Sullivan et al. . |
| 4,620,546 | 11/1986 | Aida et al. . |
| 4,930,496 | 6/1990 | Bosley, Jr. ............... 601/4 |
| 4,955,385 | 9/1990 | Kvalo et al. ............... 601/4 |
| 5,081,997 | 1/1992 | Bosley, Jr. et al. . |
| 5,161,536 | 11/1992 | Vilkomerson et al. . |
| 5,234,004 | 8/1993 | Hascoet et al. ............... 607/102 |

FOREIGN PATENT DOCUMENTS

| | | |
|---|---|---|
| 2660543 | 10/1991 | France . |
| WO91/13650 | 9/1991 | WIPO . |
| WO92/04934 | 4/1992 | WIPO . |
| WO92/15253 | 9/1992 | WIPO . |

*Primary Examiner*—Ruth S. Smith
*Attorney, Agent, or Firm*—Hill, Steadman & Simpson

[57] ABSTRACT

A catheter which is provided for employment in the treatment of pathological tissue in a patient by charging with heating radiation, whereby the treatment ensues under diagnostic ultrasound monitoring and the catheter has at least one acoustic marking member attached in the region of its distal end for marking tissue not to be treated. The marking member has an acoustic impedance deviating from that of the surrounding tissue.

27 Claims, 3 Drawing Sheets

SYSTEM FOR THE TREATMENT OF PATHOLOGICAL TISSUE HAVING A CATHETER WITH A MARKER FOR AVOIDING DAMAGE TO HEALTHY TISSUE

BACKGROUND OF THE INVENTION

1. Field Of the Invention

The present invention is directed to a system for treatment of pathological tissue in a patient by charging a region containing the pathological tissue with heating radiation by means of a catheter.

2. Description of the Prior Art

It is known to treat pathological tissue by heating the pathological tissue, for example, with microwaves or ultrasound waves that are generated with suitable sources. To the extent that the resulting tissue temperatures lie below 45° C., the cell metabolism is disturbed with the consequence that growth is slowed in the case of tumors or a regression of the tumor even occurs. This type of treatment is known as local hyperthermia. When temperatures above 45° C. are reached, the cell protein coagulates, with the consequence that the tissue is necrotized. The latter type of treatment is referred to as thermotherapy.

In order to avoid the unintentional treatment of healthy tissue in the case of local hyperthermia and to avoid the unintentional necrotization of healthy tissue in the case of thermotherapy, suitable measures must be undertaken. In this context, U.S. Pat. No. 4,620,546 discloses that the region to be heated with a therapeutic ultrasound source be localized by detecting harmonics of the therapeutic ultrasound emitted by the therapeutic ultrasound source from the output signal of a diagnostic ultrasound transducer, and the position of the heated region identified on this basis is mixed into the ultrasound image. It is also known, for example from WO 91/13650, to bring a catheter into the region of the pathological tissue in a suitable way and to monitor the resulting temperatures with a temperature sensor integrated into the catheter. For protecting healthy tissue, moreover, the catheter can have a coolant flowing through it. Nonetheless, an unintentional treatment or necrotization of healthy tissue cannot be reliably precluded. In particular, the necrotization of healthy tissue can lead to a serious injury to the patient. In the treatment of benign prostate hyperplasia (BPH), for example, there is thus the risk of injury to one or both bladder sphincters. An injury to the outer sphincter (sphincter externus) leads to incontinence of the patient; injury to the inner sphincter (sphincter internus) deteriorates the procreative capability of the patient as a consequence of retrograde ejaculation.

SUMMARY OF THE INVENTION

An object of the present invention is to provide a system for the treatment of pathological tissue with heating radiation by means of a catheter such that the risk of unintentional vesication, particularly necrotization of tissue due to heating radiation, is at least diminished if not completely avoided.

This object is inventively achieved in a therapy system having a catheter which is provided for employment in the treatment of pathological tissue in a patient together with an extra corporeal applicator for charging the pathological tissue with heating radiation, whereby the treatment ensues under diagnostic monitoring on the basis of image data acquired with a diagnostics installation which measures local differences in the body of the patient with respect to at least one characteristic physiological (physical or chemical) quantity. The catheter has at least one marking member attached in the region of its distal end that differs in view of at least one characteristic quantity of the tissue surrounding it in the treatment so that it can be placed on the basis of the image data so as to be located in the region of tissue not to be treated. Before beginning the treatment, the catheter is placed directly or with the aid of monitoring by the diagnostics installation, so that the marking member is known to be located in the region of tissue whose vesication is to be precluded. When, with monitoring on the basis of the diagnostic installation, the treatment is then begun by extracorporeally charging the pathological tissue with heating radiation, the marking member is clearly displayed in the image of the diagnostics installation since it differs from the surrounding tissue in view of at least one characteristic quantity taken into consideration by the diagnostics installation in the imaging. The personnel conducting the treatment can then without difficulty avoid charging the tissue region marked by the marking member with the heating radiation. The position of the marking member in the image of the diagnostics installation (which can, for example, be an x-ray system or a magnetic resonance imaging system) can be acquired in an electronic fashion in a known way. When, moreover, the spatial position of the diagnostics installation and of the patient to be treated are known relative to one another (this position, for example, can be acquired with the assistance of position sensors), then the spatial position of the marking member can be calculated. It is then possible without further difficulty to manually or automatically control the motion of the source of the heating radiation and of the body of the patient relative to one another such that a charging of the region marked by the marking member with heating radiation is avoided.

A catheter having a distal end region composed of a material that differs from the surrounding tissue in view of its acoustic impedance in order to facilitate the localization of the catheter in an image generated with a diagnostic ultrasound means, moreover, is disclosed by U.S. Pat. No. 5,081,997.

According to an embodiment of the invention which is preferred because of its uncomplicated nature, the diagnostics installation is an ultrasound imaging system and the marking member differs from the surrounding tissue in terms of its acoustic impedance. It is then assured that the marking member is highly visible in the ultrasound images.

A further object of specifying a catheter that is especially suited for treatment of prostate conditions, for example of benign prostate hyperplasia or of prostate carcinoma, is achieved in an embodiment wherein the catheter is adapted for introduction into the urethra and has two acoustic marking members that are arranged at a distance from one another along the catheter, this distance corresponding to the distance between the sphincter externus and sphincter internus of the patient to be treated. Injury to the sphincters can thus be easily avoided, since these are exactly marked. The distance between the two sphincters can be easily identified in a known way from the ultrasound image.

In order to adapt the spacing of the marking members to individual requirements, in a further version of the invention the distance between the marking members is variable. There is also the possibility, however, of keeping a plurality of catheters on hand, each of which has a different spacing between the marking members, whereby the spacing, for example, can be graduated in steps of 2 millimeters each.

In order to facilitate the positioning of the catheter, an expandable balloon is provided at the distal end of the catheter in a further version of the invention. This expandable balloon is disposed a distance from the marking member neighboring it which is equal to the average distance of the inside of the urinary bladder from the sphincter internus. One then proceeds in the catheterization by first introducing the catheter with the balloon to such an extent that it is situated within the urinary bladder. Subsequently, the balloon is expanded and the catheter is withdrawn to such an extent that that side of the balloon facing away from the distal end of the catheter comes to be placed against the inside wall of the urinary bladder. The marking member neighboring the distal end of the catheter is then located inside the sphincter internus, whereas the other marking member is located inside the sphincter externus when the spacing of the marking members from one another is correctly selected or set. The positioning of the catheter can be easily monitored in the ultrasound image.

In another embodiment of the invention the catheter has a coolant flowing through it during operation, so that injury to healthy tissue adjoining the catheter is practically precluded in the case of benign prostate hyperplasia of the urethra.

In a further embodiment of the invention the catheter has at least one temperature sensor and/or at least one pressure sensor in the region of its distal end, preferably between the marking members, so that a qualitative acquisition of the temperature and/or acoustic pressure occurring in the region of the tissue to be treated is possible. Respective catheters having an integrated ultrasound transducer that, however, does not serve the purpose of measuring pressure, or having an integrated temperature sensor, moreover, are known from U.S. Pat. No. 5,161,536 and U.S. Pat. No. 4,497,324 in another context.

DESCRIPTION OF THE PREFERRED EMBODIMENTS

Figure 1:
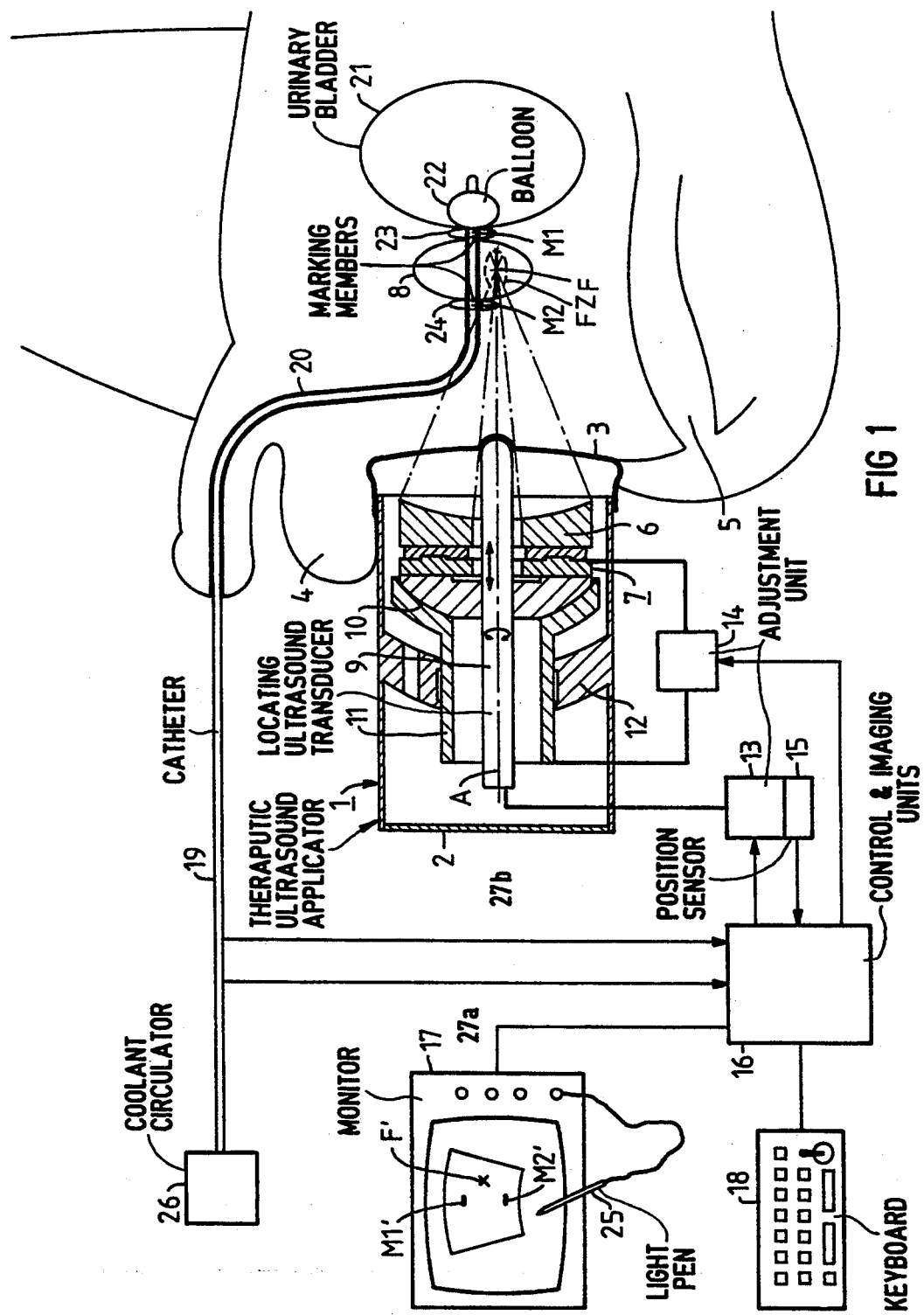
FIG. 1 is a schematic illustration of a longitudinal section through the body of a patient and a therapy system having a catheter constructed and operating in accordance with the principles of the present invention.

FIG. 1 shows the invention in the embodiment of a therapy system for treating benign prostate hyperplasia, which has a source of heating radiation, namely an extracorporeal therapeutic ultrasound applicator 1. The ultrasound applicator 1 has a tubular housing 2 that is filled with a liquid acoustic propagation medium, for example water, and has an application end closed with a flexible coupling membrane 3. The membrane 3 serves the purpose of coupling the ultrasound applicator 1 to the body surface of a patient to be treated. In the example of FIG. 1, the applicator 1 is acoustically coupled in the region of the perineum, i.e. between scrotum 4 and rectum 5 of the patient P. For acoustic coupling, the coupling membrane 3 of the ultrasound applicator 1 is pressed against the body surface of the patient P.

An ultrasound resonator 6 having an emission surface of a concave, spherically curved shape, is located in the inside of the housing 2. The ultrasound resonator 6 is attached to a carrying member composed of several parts that is generally referenced 7. The ultrasound resonator 6 is constructed in a known way, i.e. the ultrasound resonator 6 can be a single, appropriately shaped piezo ceramic member; the ultrasound transducer 6, however, can also be composed of a plurality of small piezo ceramic transducers arranged mosaically. In both instances, a backing (supporting member) having a suitable thickness can be provided in a known way that is not shown, this backing being formed of a material having a suitable acoustic impedance.

The ultrasound resonator 6 has an acoustic axis A along which the generated ultrasound waves propagate. The ultrasound waves converge in a focus F, which is the center of the spherically curved emission surface of the ultrasound resonator 6. A focus zone FZ that is indicated with broken lines in FIG. 1 surrounds the focus F. The focus zone FZ, which corresponds to the effective therapeutic region of the ultrasound waves, is that zone within which the peak pressure of the ultrasound waves is no lower than half the peak pressure maximally occurring in the focus zone FZ ($-6$ dB zone). The drive of the ultrasound resonator 6 ensues with an electric generator contained in a control and imaging unit which is described below.

An ultrasound locating transducer 9, preferably a B-scan applicator, is accepted in a bore of the carrying member 7, this ultrasound locating transducer 9 serving the purpose of locating the region to be treated, i.e. the prostate 8. In order to be able to align the ultrasound locating transducer 9 relative to the prostate 8 such that a good image is obtained, the ultrasound locating transducer 9 is accepted longitudinally displaceable and rotatable in the bore of the carrying member 7, this being indicated in FIG. 1 by corresponding arrows. During operation of the ultrasound locating transducer 9, it lies against the body surface of the patient P with the coupling membrane 3 therebetween for a good image quality.

As may be seen from FIG. 1, the side of the carrying member 7 facing away from the ultrasound resonator has a spherically curved bearing surface 10 that cooperates with a spherically cap-shaped bearing surface of a corresponding radius in a bearing member 11, that is accepted longitudinally displaceable but non-rotatably in the bore of a housing flange 12. The center of the bearing surface 10 is different from the focus F. It is thus possible to spatially modify the alignment of the ultrasound resonator 6 and of the ultrasound locating transducer 9 relative to the body of the patient P without a relative motion occurring between the coupling membrane 3 and the body surface of the patient P.

Adjustment units 13 and 14 are provided for adjusting the ultrasound locating transducer 9 relative to the carrying member 7 and for adjusting the carrying member 7 having the ultrasound resonator 6 relative to the housing 2 and relative to the coupling membrane 3. This latter adjustment possibility serves the purpose of displacing the focus zone FZ and the patient relative to one another. The adjustment unit 13 and 14 are schematically indicated in FIG. 1 and are preferably motor-driven adjustment units. A position sensor 15 schematically indicated in FIG. 1 is allocated to the adjustment unit 13. This position sensor 15 provides signals corresponding to the momentary position of the ultrasound locating transducer 9 relative to the carrying member 7. Both the adjustment units 13 and 14 and the position sensor 15 are connected to a control and imaging unit 16 to which a monitor 17 and a keyboard 18 are connected. The control and imaging unit 16 cooperates with the ultrasound locating transducer 9 in a known way as an imaging diagnostics installation for generating image information, namely ultrasound B-images, with the current ultrasound image being displayed on the monitor 17. The arrangement of the ultrasound locating transducer 9 relative to the ultrasound resonator 6 is selected such that the acoustic axis A of the ultrasound resonator 6 lies in the body slice of the patient P shown in the ultrasound B-image. Taking the output signal of the position sensor 15 into consideration, the control and imaging unit 16 mixes a mark F' into the ultrasound image, this mark F' identifying the current position of the center of the focus zone FZ.

In addition to containing the image-generating electronics required for producing ultrasound images, the control and imaging unit 16 contains all circuits that are required for driving the adjustment units 13 and 14 as well as for driving the ultrasound resonator 6.

FIG. 1 also shows a catheter 19 that is introduced into the urethra 20 of the patient P for the implementation of a treatment, such that the distal end of the catheter 19 projects into the urinary bladder 21. The catheter 19 has an expandable balloon 22 at its distal end. When the distal end of the catheter 19 is advanced into the urinary bladder 21, the balloon 22 is inflated. Subsequently, the catheter is retracted such that the balloon 22 presses against the region of the inside wall of the urinary bladder 21 surrounding the opening of the urethra 20. The region of the distal end of tile catheter 19, namely between the balloon 22 and the proximal end, is provided with two acoustic marking members M1 and M2. The acoustic marking members M1 and M2 have a spacing from one another that essentially corresponds to the distance between the sphincter internus 23 and the sphincter externus 24 of the patient P to be treated, whereby the distance between the acoustic marking member M1 and the side of the balloon 22 facing it has a spacing that identically corresponds to the spacing of the inside of the urinary bladder 21 from the sphincter internus that is averaged over the patient population. The acoustic marking members M1 and M2 are formed of a material, for example stainless steel, whose acoustic impedance (=speed of sound times density of the respective medium) deviates from that of the tissue surrounding the catheter 19 (or the marking members M1 and M2) in tile treatment. Since, as a consequence of the different acoustic impedances, the diagnostic ultrasound waves emanating from the ultrasound locating transducer 9 are reflected at the boundary surfaces between the marking members M1 and M2 as well as the surrounding tissue, images M1' and M2' corresponding to the marking members M1 and M2 are consequently clearly visible in the ultrasound image.

For implementing a treatment, one proceeds by applying the coupling membrane of the ultrasound applicator 1 to the perineum of the patient P to be respectively treated, who preferably assumes what is referred to as the lithotomy position. The coupling ensues so that no air bubbles are enclosed between the body surface and the coupling membrane 3. Thereupon, the production of ultrasound images is started by appropriate actuation of the keyboard 18. Likewise by appropriate actuation of the keyboard, the adjustment units 13 and 14 are now actuated such that an alignment of the ultrasound locating transducer 9 relative to the body of the patient P is obtained wherein the prostate 8 is clearly imaged in the ultrasound image. The distance between the two sphincters is now identified and displayed on the monitor 17 by the control and imaging unit 16 in a known way, for example by marking the sphincter internus 23 and the sphincter externus 24 in the ultrasound image with a light pen 25. Subsequently, a catheter 19 whose marking members M1 and M2 have a spacing from one another that essentially corresponds to the spacing between the two bladder sphincters of the patient to be treated, is selected from a stock of catheters 19 whose respective marking members M1 and M2 have different spacings from one another. This catheter 19 is now introduced into the urethra 20 of the patient P and is positioned with the assistance of the balloon 22 such that the marking members M 1 and M2 are located in the region of tissue that is not to be heated, i.e. inside the sphincter internus 23 and, respectively, the sphincter externus 24.

A region of the prostate 8 to be treated can now be marked in the ultrasound image with the light pen 25 or with a similar input means. In response to an appropriate actuation of the keyboard 18, the control and imaging unit 16 now actuates the adjustment unit 14 such that the focus zone FZ is displaced into that region of the prostate 8 that corresponds to the region marked with the light pen 25. This is shown in the ultrasound image in that the mark F' comes into coincidence with the region marked with the light pen 25 after the actuation of the adjustment unit 14 has been carried out. When this is the case, the control and imaging unit 19 drives the ultrasound resonator 6 to generate ultrasound. Continuous sound is emitted over a time span that is selected such that the temperature required for the necrotization of tissue, which usually lies beyond 45° C., is exceeded.

Thereupon, a region of the prostate 8 to be treated can again be marked with the light pen 25 and can be treated in the described way. The risk that the sphincter internus 23 or, respectively, sphincter externus 24 will be injured or destroyed in this procedure, with the consequence of a deterioration of the procreative ability or, respectively, of incontinence, is less than slight, since the two bladder sphincters have their position clearly identified in the ultrasound image by the clearly perceptible images M1' and M2' of the marking members M1 and M2.

Moreover, there is also the possibility of tracing the contours of a region of the prostate 8 to be treated with the light pen 25 in the ultrasound image. In response to an appropriate actuation of the keyboard 18, the focus zone FZ is then displaced step-by-step within the region traced with the light pen 25 upon activation of the ultrasound resonator 6 such that the entire traced region is charged with ultrasound waves and is necrotized. Here, too, the risk that a region of treatment marked with the light pen 25 that mistakenly contains one or both bladder sphincters is inconceivably slight.

Moreover, there is also the possibility of entering a defined spacing as a minimum distance of the focus zone FZ from the marking members M1 and M2, this being entered via the keyboard 18 that then serves as the input unit. The control and imaging unit 16 then actuates the adjustment unit 14 such that the focus zone FZ (regardless of whether it is a region marked with the light pen 25 in the above-described way or a region traced with the light pen 25) nowhere approaches the marking members M1 and M2 to such an extent that the defined distance is downwardly transgressed. This is even true when the input undertaken with the light pen 25 would demand a downward transgression of the defined distance in and of itself. In this operating mode, the risk of injury to the sphincters is practically precluded.

The ultrasound imaging, moreover, preferably essentially ensues in real time, i.e. a plurality of ultrasound images are produced per second. Otherwise, the ultrasound imaging must ensue in such a way that its is assured that the current ultrasound image in fact makes all information required for the respective treatment phase available.

In order to preclude damage to the urethra 20, it is provided that a coolant flows through the catheter 19. The corresponding coolant circulator 26 is shown in FIG. 1, which also serves as a heat exchanger. In order to be able to monitor the therapy process, at least one pressure sensor and one temperature sensor are arranged in the region of the distal end of the catheter 19 between the marking members M1 and M2. The output signals supplied by these sensors are supplied to the control and imaging unit 16, this being illustrated in FIG. 1 by schematically indicated lines 27a and 27b. The evaluation of the output signals of the sensors is assumed by the control and imaging unit 16 which also mixes the measured pressure and temperature values into the ultrasound image. Further details regarding the cooling and the arrangement of the sensors shall be set forth in conjunction with FIG. 3.

Figure 2:
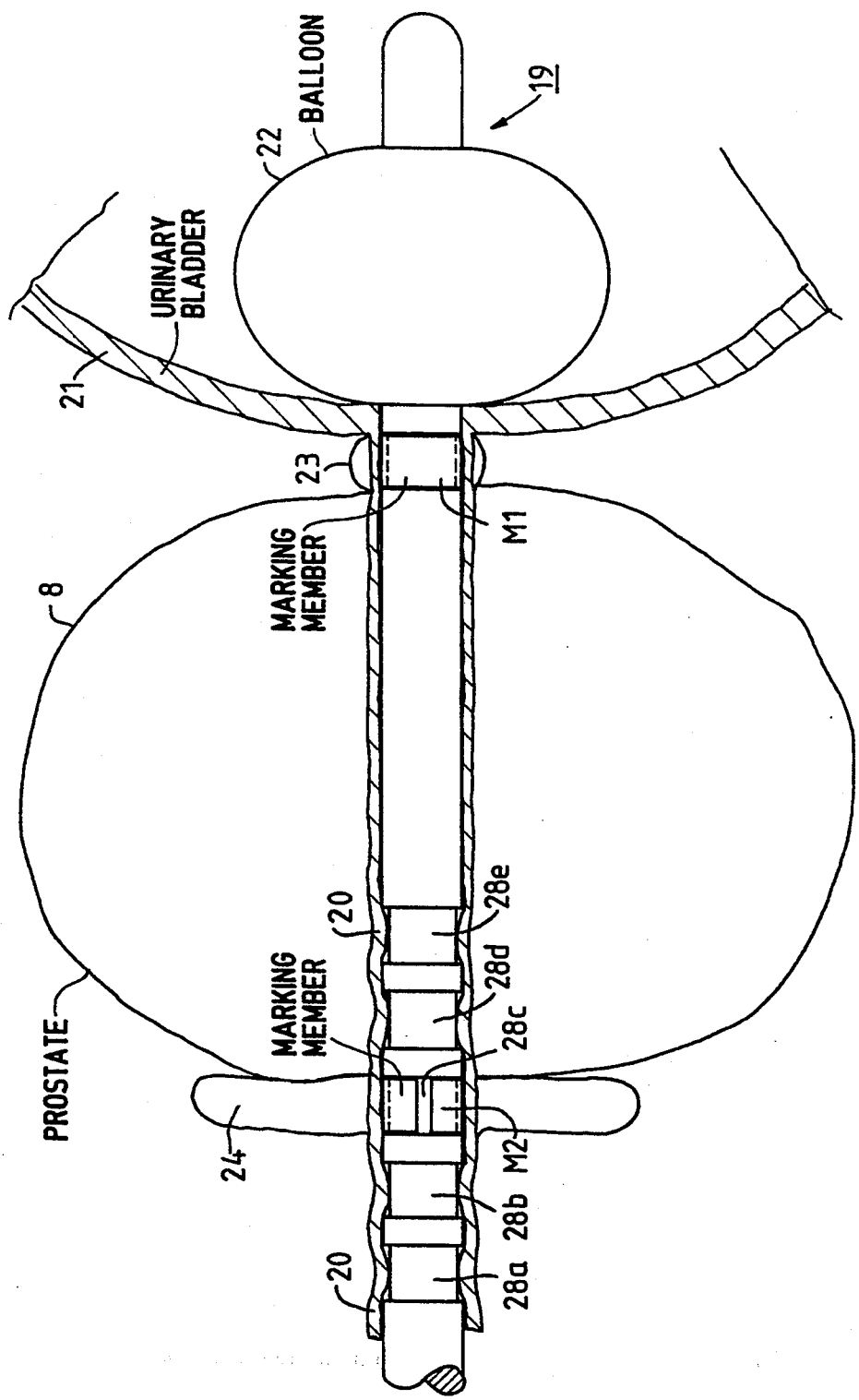
FIG. 2 is an enlarged, schematic illustration of the distal end of the catheter of FIG. 1 introduced into the body of the patient together with the surrounding organs.

FIG. 2 shows a catheter 19, which differs from that set forth in conjunction with FIG. 1 to the extent that the spacing of the marking members M1 and M2 from one another is variable. This is achieved in that the marking member M2, which serves the purpose of marking the sphincter externus 24, is executed as a slotted ring that can be snapped into a plurality of annular grooves 28a through 28e that are introduced into the outside generated surface of the catheter 19. Each of the grooves 28a through 28e is disposed a different distance from the marking member M1, so that its is possible to snap the marking member M2 into that groove from among the grooves 28a through 28e whose distance from the marking member M1 corresponds or comes closest to the distance present between the sphincter internus 23 and sphincter externus 24 in the patient to be treated. In FIG. 2, moreover, the urethra 20 and the urinary bladder 21 are shown, but other tissue is omitted for clarity.

Figure 3:
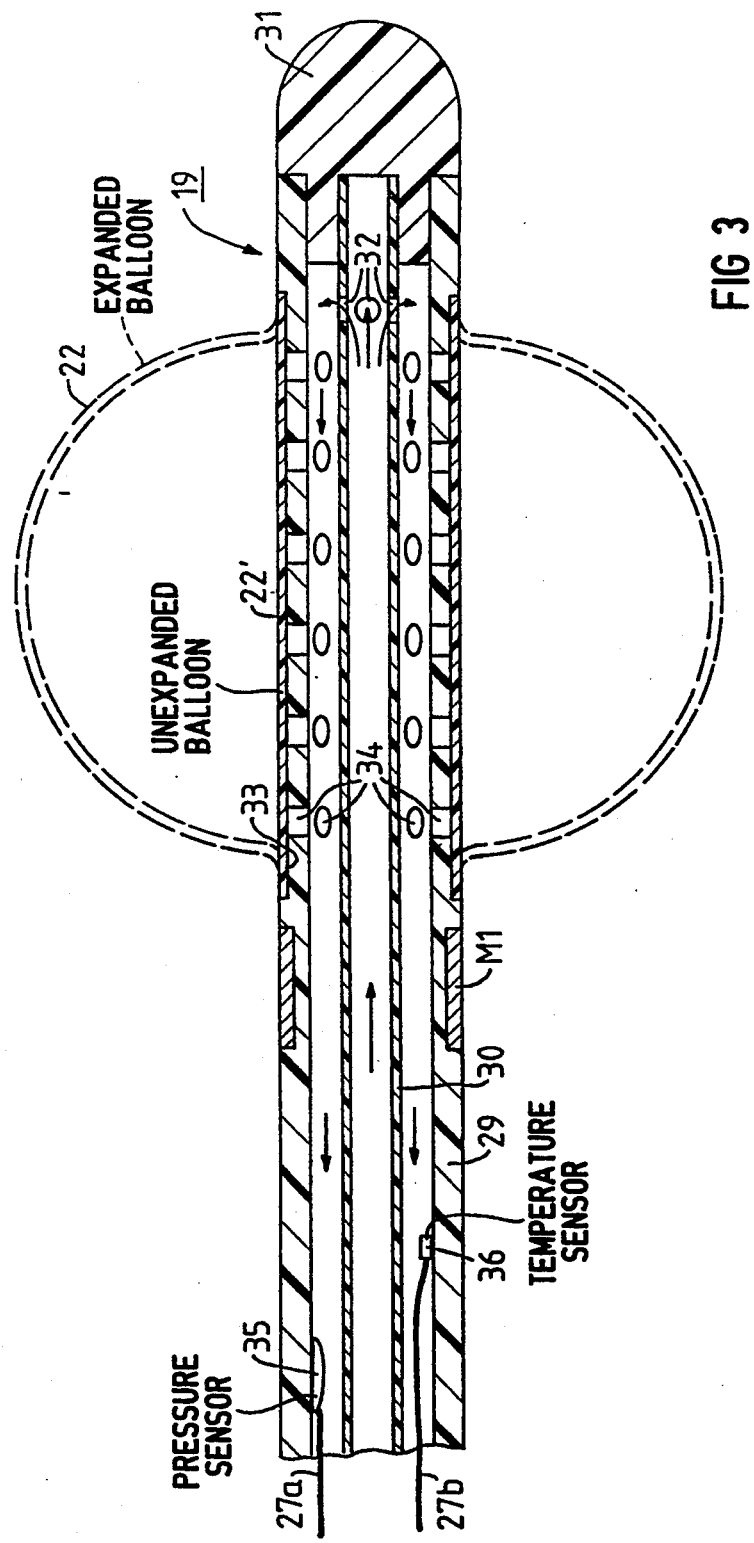
FIG. 3 is a longitudinal section through the distal end of the catheter of FIG. 2.

The structure of the catheter 19 in the region of its distal end may be seen in detail in FIG. 3. The catheter 19 is biluminar, having a flexible, outer catheter tube 29 in which an inner catheter tube 30 that is likewise flexible is coaxially arranged. A closure part 31 formed by a rounded-off introduction end is provided at the distal end; this closure part 31 closes the outer catheter tube 29 liquid-tight. The inner catheter tube 30 is accepted liquid-tight in a bore of the closure part 31. Just before the closure part 31, the inner catheter tube 30 has a plurality of flow-through openings 32 that produce a connection between the inner lumen surrounded by the inner catheter tube 30 and the outer lumen situated between the outer catheter tube 29 and the inner catheter tube 30. A preferably liquid coolant can be caused to flow through the catheter 19 with the coolant circulator 26 in the way indicated by the arrows in FIG. 3.

A channel 33 that accepts a flexible balloon part 22' is introduced into the outer generated surface of the outer catheter tube 29 between the closure part 31 and the marking member M1. This flexible balloon part 22' has the region of its two ends connected liquid-tight to the outer catheter tube 29, for example by gluing. As long as the pressure of the coolant flowing through the catheter 19 does not exceed a limit value, the balloon part 22' has the shape shown with solid lines in FIG. 3 wherein it presses against the channel 33. Since a plurality of openings 34 penetrating the wall of the outer catheter tube 29 are provided in the region of the channel 33, however, there is the possibility of expanding the balloon part 22' into the balloon 22 by increasing the pressure of the coolant in the way indicated with broken lines in FIG. 3.

A pressure sensor 35 and a temperature sensor 36 are applied to the inside wall of the outer catheter tube 29 at that side of the marking member M1 facing away from the balloon 22; these sensors are in communication with the control and imaging unit 16 via the schematically indicated lines 27a and 27b.

Silicone rubber, for example, is suitable as material for the inner catheter tube 29, for the outer catheter tube 30 and for the closure part 31.

The above-described exemplary embodiment is directed to the treatment of benign prostate hyperplasia. However, other maladies can also be treated. If tumor conditions are to be treated, the regions to be treated are only heated to such an extent that a disturbance of the cell metabolism ensues but the coagulation of the cell protein is suppressed. The placement of the catheter need not necessarily ensue upon utilization of natural paths. On the contrary, it can also ensue in a different way, for example endoscopically. Dependent on the condition to be treated, moreover, the catheter can also have only one or more than two marking members.

Focused ultrasound waves need not necessarily be employed as heating radiation. On the contrary, there is also the possibility of employing some other heating radiation, for example, microwaves.

Although modifications and changes may be suggested by those skilled in the art, it is the intention of the inventors to embody within the patent warranted hereon all changes and modifications as reasonably and properly come within the scope of their contribution to the art.

We claim as our invention:

1. A system for in vivo treatment of pathological tissue by charging said pathological tissue with heating radiation comprising:

diagnostic monitoring means for monitoring a region of a patient containing pathological tissue to be treated, adjacent to non-pathological tissue, by obtaining image data corresponding to localized differences in at least one characteristic physiological quantity of said patient; extracorporeal means for charging said pathological tissue with heating radiation; and a catheter adapted for introduction into said patient prior to and during the charging of said pathological tissue with said heating radiation, said catheter having a distal end which is disposed in said region when said catheter is introduced into said patient, and having marking means, disposed at said distal end and differing from tissue in said region surrounding said distal end with regard to said at least one characteristic physiological quantity, for permitting identification of said distal end of said catheter in said image data for providing an indicator in said image data to avoid damage to non-pathological tissue by said heating radiation.

2. A system as claimed in claim 1 wherein said diagnostic monitoring means comprises means for ultrasonically monitoring said region of said patient, and wherein said marking means has an acoustic impedance deviating from the acoustic impedance of the tissue surrounding said distal end of said catheter during treatment.

3. A system as claimed in claim 1 for the treatment of prostate conditions, wherein said catheter has a shape for introduction into the human urethra, and wherein said marking means comprises two acoustic marking members disposed along said catheter spaced from each other at a distance adapted to correspond to the spacing between the sphincter externus and the sphincter internus of the patient.

4. A system as claimed in claim 3 wherein said marking members are slidably mounted on said catheter permitting the spacing between said two marking members to be varied.

5. A system as claimed in claim 1 wherein said catheter further has an expandable balloon disposed at said distal end, wherein said marking means comprises at least one marking member, and wherein said expandable balloon is disposed a distance along said catheter from said marking member equal to a predetermined average distance of the inside of the urinary bladder from the sphincter internus over a patient population.

6. A system as claimed in claim 1 wherein said catheter further comprises means for circulating a coolant through said catheter during said treatment.

7. A system as claimed in claim 1 wherein said catheter has at least one temperature sensor disposed at said distal end.

8. A system as claimed in claim 1 wherein said catheter has at least one pressure sensor disposed at said distal end.

9. A system as claimed in claim 1 wherein said marking means comprises two acoustic marking members disposed a distance from each other along said catheter and wherein said catheter has a temperature sensor disposed thereon between said two acoustic marking members.

10. A system as claimed in claim 1 wherein said marking means comprises two acoustic marking members disposed a distance from each other along said catheter and wherein said catheter has a pressure sensor disposed thereon between said two acoustic marking members.

11. A system as claimed in claim 1 further comprising adjustment means for adjusting the relative position of said patient and said extracorporeal means for charging said pathological tissue with said heating radiation, based on said image data, for treating different tissue regions with said heating radiation.

12. A system as claimed in claim 11 wherein said extracorporeal means for charging said pathological tissue with said heating radiation comprises extracorporeal means for administering said heating radiation focused to a focused zone, and further comprising control means for controlling said adjustment means for maintaining a distance between said focused zone and said marking means above a predetermined dimension.

13. A system as claimed in claim 12 further comprising input means for selectively entering said predetermined dimension into said control means.

14. A method for administering heating radiation having a therapeutic region to pathological tissue in a body region of a patient, said body region and said therapeutic region being displaceable relative to each other, said method comprising the steps of:

generating image data identifying tissue in said body region to be treated with said heating radiation and adjacent tissue in said body region not to be treated by said heating radiation by acquiring localized differences with regard to at least one characteristic physiological quantity in said patient;

inserting a catheter into said patient having a distal end with a marking means at said distal end differing with respect to said at least one characteristic physiological quantity from tissue in said patient surrounding said distal end of said catheter so that said marking means is identifiable in said image data, until said marking means lies in a region of said adjacent tissue not to be treated;

generating a mark in said image data corresponding to the current position of said therapeutic region;

aligning said therapeutic region relative to said tissue to be treated so that said mark in said image data lies outside said region of tissue not to be treated and inside said tissue to be treated; and extracorporeally administering heating radiation to said tissue to be treated.

15. A method as claimed in claim 14 for treating benign prostate hyperplasia, comprising the additional steps of introducing said catheter into said patient through the urethra and placing said marking means in the region of the sphincter externus.

16. A method as claimed in claim 15 wherein said catheter has a further marking means spaced from said marking means and comprising the additional step of locating said catheter in said patient with said marking means at said sphincter externus and said further marking means at the sphincter internus.

17. A method as claimed in claim 16 comprising the additional steps of: mounting said marking means and said further marking means on said catheter so that said distance between said marking means and said further marking means is variable;

measuring the distance in a patient to be treated with said heating radiation between the sphincter externus and the sphincter internus on the basis of said image data; and setting the distance between said marking means and said further marking means on said catheter, before inserting said catheter, to equal the measured distance.

18. A method as claimed in claim 14 wherein the step of administering said heating radiation to said tissue to be treated is further defined by administering therapeutic ultrasound to said tissue to be treated.

19. A method as claimed in claim 14 wherein the step of generating image data is further defined by generating image data on the basis of diagnostic ultrasound and measuring localized differences in said patient with regard to differences in acoustic impedance of tissue.

20. A method as claimed in claim 14 wherein said catheter further has an expandable balloon disposed at said distal end, wherein said marking means comprises at least one marking member, and comprising the additional steps of:

determining an average distance of the inside of the urinary bladder from the sphincter internus over a patient population; and setting a spacing between said at least one marking member and said expandable balloon on said catheter equal to said average distance.

21. A method for administering heating radiation having a therapeutic region to pathological tissue in a body region of a patient, said patient and said therapeutic region being displaceable relative to each other, said method comprising the steps of:

generating image data identifying tissue in said body region to be treated with said heating radiation and adjacent tissue in said body region not to be treated by said heating radiation by acquiring localized differences with regard to at least one characteristic physiological quantity in said patient;

inserting a catheter into said patient having a distal end with a marking means at said distal end differing with respect to said at least one characteristic physiological quantity from tissue in said patient surrounding said distal end of said catheter so that said marking means is identifiable in said image data, until said marking means lies in a region of said adjacent tissue not to be treated;

selecting a defined distance between said marking means and said therapeutic region which must, at a minimum, be maintained during said treatment;

aligning said therapeutic region relative to said tissue to be treated using said image data to maintain at least said defined distance between said marking means and said therapeutic region; and extracorporeally administering said heating radiation to said tissue to be treated.

22. A method as claimed in claim 21 for treating benign prostate hyperplasia, comprising the additional steps of introducing said catheter through the urethra and placing said marking means in the region of the sphincter externus.

23. A method as claimed in claim 22 wherein said catheter has a further marking member spaced from said marking member and comprising the additional step of locating said catheter in said patient with said marking means at said sphincter externus and said further marking means at the sphincter internus.

24. A method as claimed in claim 23 comprising the additional steps of: mounting said marking means and said further marking means on said catheter so that said distance between said marking member and said further marking member is variable;

measuring the distance in a patient to be treated with said heating radiation between the sphincter externus and the sphincter internus on the basis of said image data; and setting the distance between said marking member and said further marking member on said catheter, before inserting said catheter, to equal the measured distance.

25. A method as claimed in claim 23 wherein the step of generating image data is further defined by generating image data on the basis of diagnostic ultrasound and measuring localized differences in said patient with regard to differences in acoustic impedance of tissue.

26. A method as claimed in claim 21 wherein the step of administering said heating radiation to said tissue to be treated is further defined by administering therapeutic ultrasound to said tissue to be treated.

27. A method as claimed in claim 20 wherein said catheter further has an expandable balloon disposed at said distal end, wherein said marking means comprises at least one marking member, and comprising the additional steps of:

determining an average distance of the inside of the urinary bladder from the sphincter internus over a patient population; and setting a spacing between said at least one marking member and said expandable balloon on said catheter equal to said average distance.

* * * * *